(12) United States Patent
Thombare et al.

(10) Patent No.: US 8,022,217 B2
(45) Date of Patent: Sep. 20, 2011

(54) COMPOUNDS SUITABLE AS MODULATORS OF HDL

(75) Inventors: Pravin S. Thombare, Ahmedabad (IN); Braj Bhushan Lohray, Ahmedabad (IN); Vidya Bhushan Lohray, Ahmedabad (IN); Pankaj Ramanbhai Patl, Ahmedabad (IN)

(73) Assignee: Cadila Healthcare Limited, Ahmedabad, Gujarat (IN)

( * ) Notice: Subject to any disclaimer, the term of this patent is extended or adjusted under 35 U.S.C. 154(b) by 407 days.

(21) Appl. No.: 12/374,089

(22) PCT Filed: Jul. 27, 2007

(86) PCT No.: PCT/IN2007/000321
§ 371 (c)(1), (2), (4) Date: Feb. 6, 2009

(87) PCT Pub. No.: WO2008/059513
PCT Pub. Date: May 22, 2008

(65) Prior Publication Data
US 2009/0171091 A1 Jul. 2, 2009

(30) Foreign Application Priority Data
Jul. 31, 2006 (IN) .......................... 1213/MUM/2006

(51) Int. Cl.
*C07D 215/38* (2006.01)
(52) U.S. Cl. ...................................... 546/165; 546/166
(58) Field of Classification Search .................. 546/165, 546/166
See application file for complete search history.

(56) References Cited

U.S. PATENT DOCUMENTS

| | | | |
|---|---|---|---|
| 3,950,393 A | 4/1976 | Keck et al. | |
| 5,576,335 A | 11/1996 | Sueda et al. | |
| 5,728,835 A | 3/1998 | Aoki et al. | |
| 6,096,924 A | 8/2000 | Studer et al. | |
| 2002/0019414 A1 | 2/2002 | Altmann et al. | |
| 2004/0260075 A1 | 12/2004 | Araki | |
| 2005/0059810 A1 | 3/2005 | Maeda et al. | |
| 2006/0030613 A1 | 2/2006 | Conte-Mayweg | |
| 2006/0079677 A1 | 4/2006 | Gallet et al. | |
| 2007/0004774 A1 | 1/2007 | Dalvie et al. | |
| 2007/0185113 A1 | 8/2007 | Faeh et al. | |
| 2007/0185182 A1 | 8/2007 | Conte et al. | |
| 2007/0219261 A1 | 9/2007 | Conte et al. | |

FOREIGN PATENT DOCUMENTS

| | | |
|---|---|---|
| EP | 0665216 A1 | 8/1995 |
| EP | 00881220 A1 | 12/1998 |
| EP | 1262176 A1 | 12/2002 |
| EP | 1533292 A1 | 5/2005 |
| WO | WO-9636597 A1 | 11/1996 |
| WO | WO-0027820 A1 | 5/2000 |
| WO | WO-2004050650 A1 | 6/2004 |
| WO | WO-2004069843 A1 | 8/2004 |
| WO | WO-2005033082 A2 | 4/2005 |
| WO | WO-2006013048 A1 | 2/2006 |
| WO | WO-2007090749 A2 | 8/2007 |
| WO | WO-2007090750 A1 | 8/2007 |
| WO | WO-2007090752 A1 | 8/2007 |

OTHER PUBLICATIONS

Fusco, abstract only CA 85:142220, abstract of Gazzetta CHimica Italiana, VOl 106(1-2), pp. 85-94, 1976.*
Seto, C.T. and Whitesides, G.M., "Molecular Self-Assembly through Hydrogen Bonding . . . ", J. Am. Chem. Soc., 1993, 905-916, 115, American Chemical Society, USA.
Mathias, J.P., et al., "Self-Assembly through Hydrogen Bonding . . . ", J. Am. Chem. Soc., 1994, 1725-1736, 1994, American Chemical Society, USA.
Clayden, Jonathan, et al., "Conformational Communications between the Ar-Co and Ar-N axes . . . ", Org. Biomol. Chem., 2006, 2106-2118, The Royal Society of Chemistry.

* cited by examiner

*Primary Examiner* — D M Seaman
(74) *Attorney, Agent, or Firm* — IpHorgan Ltd.

(57) ABSTRACT

Disclosed herein in the embodiments of the present invention are the compounds suitable as modulators of HDL having general formula (1), novel intermediates involved in their synthesis, their pharmaceutically acceptable salts and pharmaceutical compositions containing them. The present invention also relates to a process of preparing compounds of general formula (1), their tautomeric forms, their pharmaceutically acceptable salts, pharmaceutical compositions containing them, and novel intermediates involved in their synthesis.

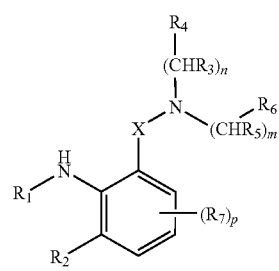

(1)

13 Claims, No Drawings

COMPOUNDS SUITABLE AS MODULATORS OF HDL

CROSS-REFERENCE TO RELATED APPLICATIONS

This is a National Phase of PCT Patent Application No. PCT/IN2007/000321, filed on Jul. 27, 2007, (published as WO 2008/059513), which in turn relies for Paris Convention priority on Indian Patent Application No. 1213/MUM/2006, filed on Jul. 31, 2006, both applications being incorporated by reference as if fully set forth herein.

FIELD OF INVENTION

The present invention relates to novel compounds suitable as modulators of HDL having general formula (1), novel intermediates involved in their synthesis, their pharmaceutically acceptable salts and pharmaceutical compositions containing them. The present invention also relates to a process of preparing compounds of general formula (1), their tautomeric forms, their pharmaceutically acceptable salts, pharmaceutical compositions containing them, and novel intermediates involved in their synthesis.

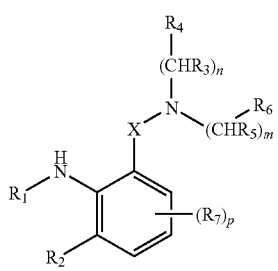

(1)

BACKGROUND TO THE INVENTION

Numerous studies have demonstrated that low plasma concentration of high density lipoprotein (HDL) cholesterol is a powerful risk factor for the development of atherosclerosis (*Atherosclerosis* 1996; 121: 1-12). HDL is one of the major classes of lipoproteins that function in the transport of lipids through the blood. The major lipids found associated with HDL include cholesterol, cholesteryl ester, triglycerides, phospholipids and fatty acids, while other classes of lipoproteins include low density lipoprotein (LDL) and very low density lipoprotein (VLDL). High LDL cholesterol and triglycerides are positively correlated, while high levels of HDL cholesterol are negatively correlated with the risk for developing cardiovascular diseases like atherosclerosis, coronary heart disease, peripheral vascular disease, stroke and the like.

Cholesteryl ester transfer protein (CETP) is a plasma protein that facilitates the movement of cholesteryl esters and triglycerides between the various lipoproteins in the blood (*Lipid Res* 1993; 34: 1255-74). Among the various factors controlling plasma levels of these disease dependent principles, CETP activity affects all three. The role of this plasma glycoprotein is to transfer cholesteryl ester and triglyceride between lipoprotein particles including HDL, LDL and VLDL. The net result of CETP activity is a lowering of HDL cholesterol and increase of LDL cholesterol, the effect of which is proatherogenic. Thus, inhibition of CETP should lead to elevation of plasma HDL cholesterol and lowering of plasma LDL cholesterol, thereby providing a therapeutically beneficial plasma lipid profile (*Medicinal Res Revs* 1993; 13: 139-59; *Pharma. Therap* 1995; 67: 443-447). 4-Carboxyamino-2-substituted 1,2,3,4-tetrahydroquinolines have been disclosed in U.S. Pat. No. 6,197,786. WO 0018721 discloses substituted polycyclic aryl and heteroalyl tertiary-heteroalkylamines with cholesteryl ester transfer protein inhibiting activity, compositions and method for treating atherosclerosis and other coronary artery diseases. WO 2005033082 discloses CETP inhibitors and metabolites. US 20050059810 disclose a novel CETP activity inhibitor dibenzylamine compound and its medicinal use. WO 2006013048 describes indole, indazole or indoline derivatives as CETP inhibitors. US2006/122224 discloses quinoline and quinoxaline compounds as CETP inhibitors. WO 2006/072362 reported the use of tetrahydroquinoline derivatives as CETP inhibitors.

Very few compounds which are modulators of CETP are there in the market and looking at the tremendous increase in life style related diseases like atherosclerosis, coronary heart attack etc. and the role CETP plays in their pathophysiological manifestation, there exists a need for providing further compounds which are modulators of the CETP protein. Surprisingly, in preliminary experiments carried out it has been found that the compounds of general formula (1), such as herein described, are modulators of HDL. Such compounds preferably, may also be suitable as inhibitors of CETP.

SUMMARY OF THE INVENTION

The present invention describes a group of novel compounds as modulators of HDL useful for the treatment of atherosclerosis, coronary heart disease and other related diseases. The novel compounds are defined by the general formula (1) below:

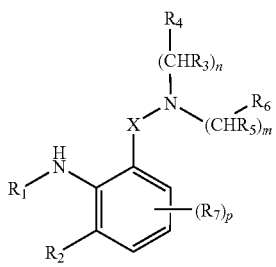

(1)

The compounds of the present invention are useful in the treatment of the human or animal body, by regulating HDL levels. The compounds of this invention are therefore suitable for the treatment of atherosclerosis and other related diseases and reducing the cardiovascular risks.

EMBODIMENTS OF THE PRESENT INVENTION

In an embodiment of the present invention is provided novel compounds of general formula (1), novel intermediates involved in their synthesis, their pharmaceutically acceptable salts, and pharmaceutical compositions containing them or their mixtures as therapeutic agents.

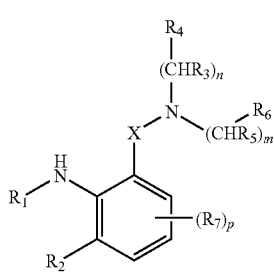

In another embodiment is provided processes for the preparation of novel compounds of general formula (1), novel intermediates involved in their synthesis, their pharmaceutically acceptable salts, and pharmaceutical compositions containing them. In a further embodiment is provided pharmaceutical compositions containing compounds of general formula (I), their pharmaceutically acceptable salts, comprising pharmaceutically acceptable carriers, solvents, diluents, excipients and other media normally employed in their manufacture.

In a still further embodiment is provided the use of the novel compounds of the present invention as lipid lowering agents, by administering a therapeutically effective and non-toxic amount of the compounds of formula (1) or their pharmaceutically acceptable compositions to the mammals.

DETAILED DESCRIPTION OF THE INVENTION

The novel compounds of the present invention are defined by the general formula (1) below:

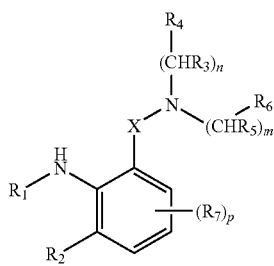

wherein X is selected from C=O or $SO_2$; $R_1$ and $R_2$ may be same or different and are each independently selected from H, optionally substituted groups selected from $C_{(1-6)}$ alkyl, $C_{(2-6)}$ alkenyl, $C_{(2-6)}$ alkynyl or a $C_{(3-7)}$ carbocyclic or a heterocycle residue or $R_1$ and $R_2$ may together along with the atoms to which they are attached form a 6-7 membered heterocyclic ring having 1-3 heteroatoms selected from N, O and S and optionally also containing double bonds; $R_3$ at each occurrence is independently selected from the group consisting of H, $COOR_8$, $CONR_8R_9$, or optionally substituted groups selected from $C_{(1-6)}$ alkyl, $C_{(2-6)}$ alkenyl, $C_{(2-6)}$ alkynyl or a $C_{(3-7)}$ carbocyclic or a heterocycle residue; $R_8$ is selected from $C_{(1-6)}$ alkyl or halo $C_{(1-6)}$ alkyl; $R_9$ is selected from H, $C_{(1-6)}$ alkyl or halo $C_{(1-6)}$ alkyl; $R_4$ is selected from an optionally substituted $C_{(3-13)}$ carbocyclic or a heterocycle residue; $R_5$ at each occurrence is independently selected from the group consisting of H, halogen, $COOR_8$, $CONR_8R_9$, $COOR_8$, or optionally substituted groups selected from $C_{(1-6)}$ alkyl, halo $C_{(1-6)}$ alkyl, $C_{(2-6)}$ alkenyl, $C_{(2-6)}$ alkynyl, $C_{(3-7)}$ carbocyclic or a heterocycle residue; $R_6$ is selected from hydrogen, optionally substituted $C_{(1-6)}$ alkyl, halo $C_{(1-6)}$alkyl, $C_{(2-6)}$ alkenyl, $C_{(2-6)}$ alkynyl, $C_{(3-13)}$ carbocyclic or a heterocycle residue; $R_7$ at each occurrence is independently selected from the group consisting of hydrogen, halogen, optionally substituted groups selected from $C_{(1-6)}$ alkyl, $COOR_8$, $CONR_8R_9$, lower halo $C_{(1-6)}$ alkyl groups;
m=1-3, n=0-2, p=0-3;

In a preferred embodiment, X is selected from C=O; $R_1$ and $R_2$ may together along with the atoms to which they are attached form a 6-7 membered heterocyclic ring having 1-3 heteroatoms selected from N, O and S and optionally also containing double bonds; $R_3$ & $R_5$ independently represent H; $R_4$ is selected from an optionally substituted aryl group; $R_5$ is H; $R_6$ is selected from optionally substituted aryl group; $R_7$ at each occurrence is independently selected from the groups comprising of hydrogen, halogen, optionally substituted groups selected from $C_{(1-3)}$ alkyl group;

In a further preferred embodiment, $R_1$ & $R_2$ together forms an optionally substituted 1,2,3,4-tetrahydro-quinoline, 3,4-dihydro-2H-benzo[1,4]oxazine, 2,3,4,5-tetrahydro-1H-benzo[b]azepine group; $R_4$ & $R_6$ are each optionally substituted phenyl group;

As used herein, "carbocycle" or "carbocyclic residue" is intended to mean any stable monocyclic or bicyclic or tricyclic ring, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5- to 7-membered monocyclic or bicyclic or 7- to 14-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7-membered monocyclic or bicyclic or 7- to 14-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Suitable substituents wherever applicable includes, but are not limited to the following radicals, alone or in combination with other radicals, hydroxyl, oxo, halo, thio, nitro, amino, alkyl, alkoxy, haloalkyl or haloalkoxy groups;

The term "substituted," as used herein, means that any one or more hydrogens on the designated atom is replaced with a selection from the indicated group, provided that the designated atom's normal valency is not exceeded, and that the substitution results in a stable compound. The term "substituted," as used herein, means that any one or more hydrogens on the designated atom is replaced with a selection from the indicated group, provided that the designated atom's normal valency is not exceeded, and that the substitution results in a stable compound.

When any variable (e.g., $R_3$) occurs more than one time in any constituent or formula for a compound, its definition at each occurrence is independent of its definition at every other occurrence. Thus, for example, if a group is shown to be substituted with 0-2 $R_3$, then said group may optionally be substituted with up to two $R_3$ groups, $R_3$ at each occurrence is selected independently from the definition of $R_3$. Also, combinations of substituents and/or variables are permissible only if such combinations result in stable compounds.

In a further embodiment the groups, radicals described above may be selected from:

the "alkyl" group used either alone or in combination with other radicals, denotes a linear or branched radical containing one to six carbons, selected from methyl, ethyl, n-propyl, iso-propyl, n-butyl, sec-butyl, tert-butyl, amyl, t-amyl, n-pentyl, n-hexyl, and the like;

The term "alkenyl" used herein, either alone or in combination with other radicals, denotes a linear or branched radical containing two to twelve carbons; such as vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl and the like. The term "alkenyl" includes dienes and trienes of straight and branched chains;

The term "alkynyl" used herein, either alone or in combination with other radicals, denotes a linear or branched radical containing two to twelve carbons, such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 4-hexynyl, 5-hexynyl, and the like. The term "alkynyl" includes di- and tri-ynes;

The term "alkoxy" used herein, either alone or in combination with other radicals, denotes a radical alkyl, as defined above, attached directly to an oxygen atom, such as methoxy, ethoxy, n-propoxy, iso-propoxy, n-butoxy, t-butoxy, iso-butoxy, pentyloxy, hexyloxy, and the like;

The term "halo" or "halogen" used herein, either alone or in combination with other radicals, such as "haloalkyl", "perhaloalkyl" etc refers to a fluoro, chloro, bromo or iodo group. The term "haloalkyl" denotes an alkyl radical, as defined above, substituted with one or more halogens; such as fluoromethyl, difluoromethyl, trifluoromethyl, fluoroethyl, difluoroethyl, trifluoroethyl, mono or polyhalo substituted methyl, ethyl, propyl, butyl, pentyl or hexyl groups. The term "haloalkoxy" denotes a haloalkyl, as defined above, directly attached to an oxygen atom, such as fluoromethoxy, chloromethoxy, fluoroethoxy chloroethoxy groups, and the like.

Suitable groups and substituents on the groups may be selected from those described anywhere in the specification.

Particularly useful compounds may be selected from but not limited to 1,2,3,4-Tetrahydro-quinoline-8-carboxylic acid (4-tert-butyl-benzyl)-(2-(4-fluoro-phenyl)-ethyl)-amide;

N-(2-{(4-tert-Butyl-benzyl)-(2-(4-fluoro-phenyl)-ethyl)-carbamoyl}-4-trifluoromethyl-phenyl)-oxalamic acid methyl ester;

N-(4-tert-Butyl-benzyl)-2-dimethylamino-N-(2-(4-fluoro-phenyl)-ethyl)-3-methyl-benzamide;

N-(2-{(4-tert-Butyl-benzyl)-(2-(4-fluoro-phenyl)-ethyl)-carbamoyl}-6-methyl-phenyl)-oxalamic acid methyl ester;

N-(4-tert-Butyl-benzyl)-2-ethylamino-N-(2-(4-fluoro-phenyl)-ethyl)-5-trifluoromethyl-benzamide;

1,2,3,4-Tetrahydro-quinoline-8-sulfonic acid (4-tert-butyl-benzyl)-(2-(4-fluoro-phenyl)-ethyl)-amide;

6-Trifluoromethyl-1,2,3,4-tetrahydro-quinoline-8-carboxylic acid (4-tert-butyl-benzyl)-(2-(4-fluoro-phenyl)-ethyl)-amide;

5-Trifluoromethyl-1,2,3,4-tetrahydro-quinoline-8-carboxylic acid (4-tert-butyl-benzyl)-(2-(4-fluoro-phenyl)-ethyl)-amide;

5-Chloro-1,2,3,4-tetrahydro-quinoline-8-carboxylic acid (4-tert-butyl-benzyl)-(2-(4-fluoro-phenyl)-ethyl)-amide;

1,2,3,4-Tetrahydro-quinoline-8-carboxylic acid (3,5-bis-trifluoromethyl-benzyl)-(2-(4-fluoro-phenyl)-ethyl)-amide;

1,2,3,4-Tetrahydro-quinoline-8-carboxylic acid (4-tert-butyl-benzyl)-(3-phenoxy-phenyl)-amide;

1,2,3,4-Tetrahydro-quinoline-8-carboxylic acid (4-tert-butyl-benzyl)-(2-(3-chloro-phenyl)-ethyl)-amide;

2,3,6,7,8,9-Hexahydro-1H-6-aza-cyclopenta(a)naphthalene-5-carboxylic acid (4-tert-butyl-benzyl)-(2-(4-fluoro-phenyl)-ethyl)-amide;

6-Methoxy-1,2,3,4-tetrahydro-quinoline-8-carboxylic acid (4-tert-butyl-benzyl)-(2-(4-fluoro-phenyl)-ethyl)-amide;

6-Methyl-1,2,3,4-tetrahydro-quinoline-8-carboxylic acid (4-tert-butyl-benzyl)-(2-(4-fluoro-phenyl)-ethyl)-amide;

1,2,3,4-Tetrahydro-quinoline-8-carboxylic acid (2-(4-fluoro-phenyl)-ethyl)-(4-trifluoromethyl-benzyl)-amide;

1,2,3,4-Tetrahydro-quinoline-8-carboxylic acid (4-diethylamino-benzyl)-(2-(4-fluoro-phenyl)-ethyl)-amide;

1,2,3,4-Tetrahydro-quinoline-8-carboxylic acid (4-tert-butyl-benzyl)-(2-(4-chloro-phenyl)-ethyl)-amide;

1,2,3,4-Tetrahydro-quinoline-8-carboxylic acid (4-tert-butyl-benzyl)-(2-(4-methoxy-phenyl)-ethyl)-amide;

1,2,3,4-Tetrahydro-quinoline-8-carboxylic acid (4-tert-butyl-benzyl)-(2-(2,6-dichloro-phenyl)-ethyl)-amide;

1,2,3,4-Tetrahydro-quinoline-8-carboxylic acid (4-tert-butyl-benzyl)-(4-fluoro-benzyl)-amide;

1,2,3,4-Tetrahydro-quinoline-8-carboxylic acid (4-tert-butyl-benzyl)-(2-(3,4-dichloro-phenyl)-ethyl)-amide;
1,2,3,4-Tetrahydro-quinoline-8-carboxylic acid (4-tert-butyl-benzyl)-(3-chloro-benzyl)-amide;
1,2,3,4-Tetrahydro-quinoline-8-carboxylic acid (4-tert-butyl-benzyl)-(2-(2-fluoro-phenyl)-ethyl)-amide;
1,2,3,4-Tetrahydro-quinoline-8-carboxylic acid (2-(3,5-bis-trifluoromethyl-phenyl)-ethyl)-(4-tert-butyl-benzyl)-amide;
6-Fluoro-1,2,3,4-tetrahydro-quinoline-8-carboxylic acid (4-tert-butyl-benzyl)-(2-(4-fluoro-phenyl)-ethyl)-amide;
6-Chloro-1,2,3,4-tetrahydro-quinoline-8-carboxylic acid (4-tert-butyl-benzyl)-(2-(4-fluoro-phenyl)-ethyl)-amide;
1,2,3,4-Tetrahydro-quinoline-8-carboxylic acid (4-tert-butyl-benzyl)-phenethyl-amide;
6,7,8,9-Tetrahydro-5H-carbazole-1-carboxylic acid (4-tert-butyl-benzyl)-(2-(4-fluoro-phenyl)-ethyl)-amide;
6-Bromo-1,2,3,4-tetrahydro-quinoline-8-carboxylic acid (4-tert-butyl-benzyl)-(2-(3-chloro-phenyl)-ethyl)-amide;
1,2,3,4-Tetrahydro-quinoline-8-carboxylic acid (4-tert-butyl-benzyl)-(2-(4-diethylamino-phenyl)-ethyl)-amide;
1,2,3,4-Tetrahydro-quinoline-8-carboxylic acid (2-(3,4-dichloro-phenyl)-ethyl)-(4-methyl-benzyl)-amide;
1,2,3,4-Tetrahydro-quinoline-8-carboxylic acid (2-(4-bromo-phenyl)-ethyl)-(4-tert-butyl-benzyl)-amide;
3,4-Dihydro-2H-benzo(1,4)oxazine-5-carboxylic acid (4-tert-butyl-benzyl)-(2-(4-fluoro-phenyl)-ethyl)-amide;
6-Methyl-1,2,3,4-tetrahydro-quinoline-8-carboxylic acid (4-tert-butyl-benzyl)-(2-(3,4-dichloro-phenyl)-ethyl)-amide;
6-Fluoro-1,2,3,4-tetrahydro-quinoline-8-carboxylic acid (4-tert-butyl-benzyl)-(2-(3,4-dichloro-phenyl)-ethyl)-amide;
1,2,3,4-Tetrahydro-quinoline-8-carboxylic acid (2-(4-fluoro-phenyl)-ethyl)-naphthalen-2-ylmethyl-amide;
1,2,3,4-Tetrahydro-quinoline-8-carboxylic acid (4-tert-butyl-benzyl)-(2-(3,4-dichloro-phenyl)-ethyl)-amide hydrochloride;
6-Chloro-1,2,3,4-tetrahydro-quinoline-8-carboxylic acid (4-tert-butyl-benzyl)-(2-(4-fluoro-phenyl)-ethyl)-amide hydrochloride;
6-Methyl-1,2,3,4-tetrahydro-quinoline-8-carboxylic acid (4-tert-butyl-benzyl)-(2-(3,4-dichloro-phenyl)-ethyl)-amide hydrochloride;
6-Fluoro-1,2,3,4-tetrahydro-quinoline-8-carboxylic acid (4-tert-butyl-benzyl)-(2-(3,4-dichloro-phenyl)-ethyl)-amide hydrochloride;
6-Chloro-1,2,3,4-tetrahydro-quinoline-8-carboxylic acid (2-benzo(1,3)dioxol-5-yl-ethyl)-(4-tert-butyl-benzyl)-amide;
6-Chloro-1,2,3,4-tetrahydro-quinoline-8-carboxylic acid (4-tert-butyl-benzyl)-(2-(3,4-dichloro-phenyl)-ethyl)-amide hydrochloride;
6-Chloro-1,2,3,4-tetrahydro-quinoline-8-carboxylic acid (4-tert-butyl-benzyl)-(2-(3,4-dichloro-phenyl)-ethyl)-amide;
1,2,3,4-Tetrahydro-quinoline-8-carboxylic acid (4-tert-butyl-benzyl)-(2-naphthalen-2-yl-ethyl)-amide;
1,2,3,4-Tetrahydro-quinoline-8-carboxylic acid (4-tert-butyl-benzyl)-(2-naphthalen-1-yl-ethyl)-amide;
1,2,3,4-Tetrahydro-quinoline-8-carboxylic acid (2-benzo(1,3)dioxol-5-yl-ethyl)-(4-tert-butyl-benzyl)-amide;
1,2,3,4-Tetrahydro-quinoline-8-carboxylic acid (4-tert-butyl-benzyl)-indan-5-yl-amide;
2,3,4,5-Tetrahydro-1H-benzo(b)azepine-9-carboxylic acid (4-tert-butyl-benzyl)-(2-(3,4-dichloro-phenyl)-ethyl)-amide;
6-Chloro-1,2,3,4-tetrahydro-quinoline-8-carboxylic acid (4-tert-butyl-benzyl)-(2-(3,4-difluoro-phenyl)-ethyl)-amide;
1,2,3,4-Tetrahydro-quinoline-8-carboxylic acid (4-tert-butyl-benzyl)-(2-(3,4-difluoro-phenyl)-ethyl)-amide;
1,2,3,4-Tetrahydro-quinoline-8-carboxylic acid (4-tert-butyl-benzyl)-(2-(4-hydroxy-phenyl)-ethyl)-amide;
1,2,3,4-Tetrahydro-quinoline-8-carboxylic acid (4-tert-butyl-benzyl)-(2-(3,4-dimethoxy-phenyl)-ethyl)-amide;
1,2,3,4-Tetrahydro-quinoline-8-carboxylic acid (4-tert-butyl-benzyl)-(3-(4-fluoro-phenyl)-propyl)-amide;
6-Chloro-1,2,3,4-tetrahydro-quinoline-8-carboxylic acid (4-tert-butyl-benzyl)-(2-(4-chloro-3-fluoro-phenyl)-ethyl)-amide;
6-Chloro-1,2,3,4-tetrahydro-quinoline-8-carboxylic acid (4-tert-butyl-benzyl)-(2-(3,5-dimethoxy-phenyl)-ethyl)-amide;
6-Chloro-1,2,3,4-tetrahydro-quinoline-8-carboxylic acid (4-tert-butyl-benzyl)-(2-(3,4-difluoro-phenyl)-ethyl)-amide, hydrochloride;
6-Chloro-1,2,3,4-tetrahydro-quinoline-8-carboxylic acid (4-tert-butyl-benzyl)-(3-(3,4-dichloro-phenyl)-propyl)-amide hydrochloride;
1,2,3,4-Tetrahydro-quinoline-8-carboxylic acid (4-tert-butyl-benzyl)-(2-(4-trimethylsilanyloxy-phenyl)-ethyl)-amide;
6-Chloro-1,2,3,4-tetrahydro-quinoline-8-carboxylic acid (4-tert-butyl-benzyl)-(2-(4-chloro-3-fluoro-phenyl)-ethyl)-amide hydrochloride;
6-Chloro-1,2,3,4-tetrahydro-quinoline-8-carboxylic acid (4-tert-butyl-benzyl)-(2-(3-chloro-4-fluoro-phenyl)-ethyl)-amide hydrochloride;
6-Chloro-1,2,3,4-tetrahydro-quinoline-8-carboxylic acid 4-tert-butyl-benzylamide;
N-(4-tert-Butyl-benzyl)-2-dimethylamino-N-[2-(4-fluoro-phenyl)-ethyl]-3-methyl-benzamide;
N-(4-tert-Butyl-benzyl)-2-(cyclohexylmethyl-amino)-N-[2-(4-fluoro-phenyl)-ethyl]-benzamide;
1,2,3,4-Tetrahydro-quinoline-8-sulfonic acid (4-tert-butyl-benzyl)-[2-(4-fluoro-phenyl)-ethyl]-amide.

The compounds of the present invention may be prepared using the methods described below, together with conventional techniques known to those skilled in the art of organic synthesis, or variations thereon as appreciated by those skilled in the art. Referred methods include, but are not limited to those described below, where all symbols are as defined earlier.

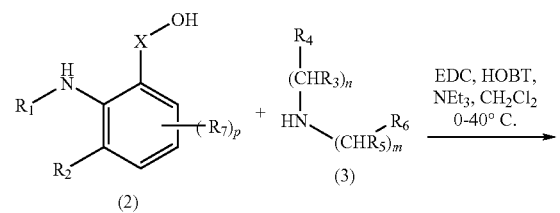

-continued

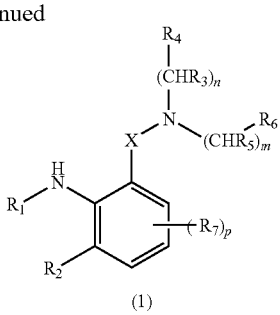

(1)

The process comprises reacting a suitable acid (X is C=O) of formula (2) wherein $R_1$, $R_2$ and $R_7$ are as described earlier, with suitably substituted secondary amine of formula (3) wherein $R_3$, $R_4$, $R_5$ and $R_6$, m, n & p are as defined earlier, in the presence of 1-hydroxybenzotriazole hydrate (HOBT) and 1-(3-dimethylaminopropyl)-3-ethylcarbodiimide hydrochloride (EDCI) and organic base such as triethyl amine, ethyl diisopropyl amine, pyridine and like to get the compound of formula (1). Reaction may be performed at 0-40° C. using solvents selected from etheral solvents like diethyl ether, THF and the like or halogenated solvents like dichloromethane, dichloroethane & the like or mixture thereof. In the case of compound of formula (1) when $R_1$ and $R_2$ combine to form partially unsaturated or fully unsaturated ring, the ring may be reduced with suitable reducing agent(s) like sodium borohydride, sodium cyanoborohydride and like in the presence of organic acid like acetic acid, trifluoroacetic acid and the like or mixture thereof at 18-25° C. to get the saturated analogue of compound of formula (1).

The pharmaceutically acceptable salts forming a part of this invention may be prepared by treating the compound of formula (1) with suitable acids in suitable solvents by processes known in the art.

It will be appreciated that in any of the above mentioned reactions any reactive group in the substrate molecule may be protected, according to conventional chemical practice. Suitable protecting groups in any of the above mentioned reactions are those used conventionally in the art. The methods of formation and removal of such protecting groups are those conventional methods appropriate to the molecule being protected. T. W. Greene and P. G. M. Wuts "Protective groups in Organic Synthesis", John Wiley & Sons, Inc, 1999, $3^{rd}$ Ed., 201-245 along with references therein gives such conventional methods and are incorporated herein as references.

The novel compounds of the present invention can be formulated into suitable pharmaceutically acceptable compositions by combining with suitable excipients by techniques and processes and concentrations as are well known.

The compounds of formula (1) or pharmaceutical compositions containing them are useful as HDL modulators suitable for humans and other warm blooded animals, and may be administered either by oral, topical or parenteral administration.

The pharmaceutical composition is provided by employing conventional techniques. Preferably the composition is in unit dosage form containing an effective amount of the active component, that is, the compounds of formula (1) according to this invention.

The quantity of active component, that is, the compounds of formula (1) according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

The compounds of the present invention are suitable as CETP inhibitors and are useful in the treatment of cardiovascular diseases, increasing the HDL and other related diseases and disease conditions.

The invention is explained in greater detail by the examples given below, which are provided by way of illustration only and therefore should not be construed to limit the scope of the invention.

1H NMR spectral data given in the tables (vide infra) are recorded using a 300 M spectrometer (Bruker A VANCE-300) and reported in δ scale and the J values are in Hz. Until and otherwise mentioned the solvent used for NMR is DMSO-$d_6$ using Tetramethyl silane as the internal standard.

EXAMPLE-1

1,2,3,4-Tetrahydro-quinoline-8-carboxylic acid (4-tert-butyl-benzyl)-(2-(4-fluoro-phenyl)-ethyl)-amide a) Triethylamine (169 mg, 1.6 mmol) was added to a mixture of 4-(tert-butyl-benzyl)-[2-(4-fluoro-phenyl)-ethyl]-amine (0.41 g, 1.4 mmol) and 8-quinolinecarboxylic acid (250 mg, 1.4 mmol) and HOBT (208 mg, 1.5 mmol) in 10 ml DCM at ambient temperature and stirred for about 18 hours. The reaction was quenched with water (10 ml) and extracted with DCM. The combined organic layers were washed with water and brine, dried over sodium sulfate, filtered and concentrated over vacuum to get 450 mg of crude quinoline-8-carboxylic acid (4-tert-butyl-benzyl)-[2-(4-fluoro-phenyl)-ethyl]-amide. The crude compound was column chromatographed over silica gel to give 250 mg (yield =39.6%) of purified product.

b) Sodium cyanoborohydride (NaBH$_3$CN) (85 mg, 1.2 mmol) was added gradually to the solution of quinoline-8-carboxylic acid (4-tert-butyl-benzyl)-[2-(4-fluoro-phenyl)-ethyl]-amide (220 mg, 0.45 mmol) in glacial acetic acid (5 ml) at ambient temperature. After stirring for 4 hrs, the reaction mixture was diluted with water and extracted with EtOAc. The combined organic layers were washed with water, brine and dried over sodium sulfate, filtered and concentrated in vacuum to get 150 mg of crude 1,2,3,4-tetrahydro-quinoline-8-carboxylic acid (4-tert-butyl-benzyl)-(2-(4-fluoro-phenyl)-ethyl)-amide. The desired product was purified by column chromatography to give 120 mg of syrupy compound (yield 60.04%).

1.32 (9H, s), 1.89 (2H, m), 2.74 (2H, t, J=6.24), 2.84 (2H, m), 3.27 (2H, t, J=5.31), 3.55 (2H, m), 4.48 (2H, brs), 4.83 (1H, brs), 6.48 (1H, t, J=7.44), 6.85 (2H, d, J=7.5), 6.90-6.97 (2H, m). 7.14 (3H, m), 7.35 (2H, d, J=8.16)

EXAMPLE-2

6-Chloro-1,2,3,4-tetrahydro-quinoline-8-carboxylic acid (4-tert-butyl-benzyl)-[2-(4-fluoro-phenyl)-ethyl]-amide, hydrochloride salt a) Concentrated sulfuric acid (73.83 g, 0.80 mol) was added dropwise to a vigorously stirred mixture of 2-amino-5-chloro-benzoic acid (90 g, 0.524 mol), I$_2$ (1.65 g, 6.4 mmol) in glycerol within 30 minutes, wherein the temperature of the mixture rises to 65-70° C. The mixture was then heated to 135-140° C. for 5-7 hrs giving a dark brown foaming mixture. The reaction mixture was cooled to room temperature and poured into 1500 ml of ice water. The pH of the mixture was adjusted to 6.5 by adding 25-30% ammonia solution. The precipitated compound was filtered, washed with cold water and dried over $P_2O_5$ to get brown solid of 6-chloro-quinoline-8-carboxylic acid (75 g) (Yield=68.91%).

b) 6-Chloro-quinoline-8-carboxylic acid (4-tert-butyl-benzyl)-[2-(4-fluoro-phenyl)-ethyl]-amide was prepared as per the process in example 1a using 6-chloro-quinoline-8-carboxylic acid (470 mg, 2.2 mmol) and 4-(tert-butyl-benzyl)-[2-(4-fluoro-phenyl)-ethyl]-amine hydrochloride salt (728 mg, 2.2 mmol) to get 1.0 g of crude product which has been without purification for further reaction (Yield=95.45%).

c) 6-Chloro-1,2,3,4-tetrahydro-quinoline-8-carboxylic acid (4-tert-butyl-benzyl)-[2-(4-fluoro-phenyl)-ethyl]-amide was prepared as per the procedure of example 1b using 6-chloro-1,2,3,4-tetrahydro-quinoline-8-carboxylic acid (4-tert-butyl-benzyl)-[2-(4-fluoro-phenyl)-ethyl]-amide (970 mg, 2.04 mmol) and $NaBH_3CN$ (386 mg, 6.1 mmol). Compound was purified by column chromatography over silica gel to get 530 mg of desired product as a yellow syrupy compound (Yield=53.92%).

d) 6-Chloro-1,2,3,4-tetrahydro-quinoline-8-carboxylic acid (4-tert-butyl-benzyl)-[2-(4-fluoro-phenyl)-ethyl]-amide (520 mg, 1.0 mmol) was dissolved in 10% methanolic HCL (5.0 ml) and the solution was kept under stirring at 5-10° C. for about 2 hrs. The precipitated hydrochloride salt was filtered, washed with cold MeOH and dried under vacuum to get hydrochloride salt of 6-chloro-1,2,3,4-tetrahydro-quinoline-8-carboxylic acid (4-tert-butyl-benzyl)-[2-(4-fluoro-phenyl)-ethyl]-amide (200 mg, Yield =38.8%).

1.25 (9H, m), 1.72 (2H, m), 2.68 (2H, m), 2.78 (2H, m), 3.58 (4H, m), 4.50 (2H,m), 6.64 (1H, s), 7.07 (6H, m), 7.35 (3H,d, J=7.41)

EXAMPLE-3

3,4-Dihydro-2H-benzo[1,4]oxazine-5-carboxylic acid (4-tert-butyl-benzyl)-[2-(4-fluoro-phenyl)-ethyl]-amide 3,4-Dihydro-2H-benzo[1,4]oxazine-5-carboxylic acid (4-tert-butyl-benzyl)-[2-(4-fluoro-phenyl)-ethyl]-amide was prepared as per the procedure of example 1b, using 3,4-dihydro-2H-benzo[1,4]oxazine-5-carboxylic acid (400 mg, 2.23 mmol) and 4-(tert-butyl-benzyl)-[2-(4-fluoro-phenyl)-ethyl]-amine (720 mg, 2.23 mmol) to get the desired title compound (750 mg, 1.63 mmol) (Yield=66.96%)

1.31 (9H, s), 2.85, (2H, brs) 1, 3.40 (2H, brs), 3.50 (2H, brs), 4.21 (2H, brs), 4.50 (2H, brs), 6.54 (1H, t), 6.56 (1H, d), 6.66 (1H, d), 6.96 (3H, t), 7.12 (3H, brs), 7.34 (2H,d)

EXAMPLE-4

2,3,4,5-Tetrahydro-1H-benzo[b]azepine-9-carboxylic acid (4-tert-butyl-benzyl)-[2-(3,4-dichloro-phenyl)-ethyl]-amide a) Solution of 2,3,4,5-Tetrahydro-1H-benzo[b]azepine (5 g, 34 mmol) in 1,2-dichloroethane (25 ml) was added to the solution of oxalyl chloride (6 ml, 47.61 mmol) in 1,2-dichloroethane (25 ml) at refluxing temperature within 30 minutes. Excess oxalyl chloride and 1.2-dichloroethane were distilled off under reduced pressure to get 8 g of crude oxo-(2,3,4,5-tetrahydro-benzo[b]azepin-1-yl)-acetyl chloride, which is further used in the next step.

b) 5.0 g $AlCl_3$ was added gradually over a period of 3 hrs to the refluxing solution of oxo-(2,3,4,5-tetrahydro-benzo[b]azepin-1-yl)-acetyl chloride and $CS_2$ (80 ml). The reaction was refluxed for additional 3 hrs and allowed to stand for overnight at room temperature. After decantation of the solvent, the residue cooled by an ice bath, was treated with water. The mixture was extracted with $CHCl_3$ and combined organic layers were washed with water, brine and dried over sodium sulfate filtered and concentrated over vacuum to get 6 g of 4,5,6,7-tetrahydro-azepino[3,2,1-hi]indole-1,2-dione as a red solid (Yield=88.69%).

c) 25 ml 30% $H_2O_2$ solution was added dropwise to the solution of 4,5,6,7-Tetrahydro-azepino[3,2,1-hi]indole-1,2-dione (6 g) in 5% NaOH (7.72 g/154.43 ml water) at ambient temperature within 30 minutes. The mixture was heated to 45-50° C. for 2 hrs. The insoluble material was filtered off and then acidified with concentrated with 10% HCL. The precipitated compound was filtered, washed with cold water and dried. The material obtained was crystallized in MeOH to get 3 g of pure 2,3,4,5-tetrahydro-1H-benzo[b]azepine-9-carboxylic acid (Yield=52.61%).

d) 2,3,4,5-Tetrahydro-1H-benzo[b]azepine-9-carboxylic acid (4-tert-butyl-benzyl)-[2-(3,4-dichloro-phenyl)-ethyl]-amide was prepared as per the procedure of example 1b, starting from 2,3,4,5-tTetrahydro-1H-benzo[b]azepine-9-carboxylic acid (500 mg, 2.618 mmol) and 4-(tert-butyl-benzyl)-[2-(3,4-dichloro-phenyl)-ethyl]-amine (980 mg, 2.618 mmol) to get the desired title compound (840 mg, 1.65 mmol) (Yield 63.21%).

1.42 (9H, s),1.64 (2H, bt), 1.76 (2H, bt), 2.76 (2H, brt), 2.98 (2H, brt), 3.48 (2H, brt), 4.33 (1H, brs), 6.74 (2H, brs), 7.01 (4H, brs), 7.26 (4H, brs)

The following compounds were prepared as per the processes similar to those disclosed in the above examples. Suitable modifications, alterations which may be required are well within the scope of a person skilled in the art.

EXAMPLE 5

6-Trifluoromethyl-1,2,3,4-tetrahydro-quinoline-8-carboxylic acid (4-tert-butyl-benzyl)-[2-(4-fluoro-phenyl)-ethyl]-amide 1.31 (9H, s), 1.8 (2H, t, J=5.45), 2.7 (2H, t, J=5.45), 2.85 (2H, m), 3.29 (2H, m), 3.57 (2H, m), 4.5 (2H, m), 5.22 (1H, s), 6.93-7.12 (8H, m), 7.3 (2H, d, J=8.20)

EXAMPLE 6

5-Trifluoromethyl-1,2,3,4-tetrahydro-quinoline-8-carboxylic acid (4-tert-butyl-benzyl)-[2-(4-fluoro-phenyl)-ethyl]-amide 1.31 (9H, s), 1.8 (2H, t, J=5.6 Hz), 2.8 (2H, t, J=5.81), 3.27 (2H, m), 3.61 (2H, m), 4.33 (2H, m), 4.9 (2H, m), 5.3 (1H, s), 6.80-7.26 (7H, m), 7.3 (2H, d, J=7.9)

EXAMPLE 7

5-Chloro-1,2,3,4-tetrahydro-quinoline-8-carboxylic acid (4-tert-butyl-benzyl)-[2-(4-fluoro-phenyl)-ethyl]-amide 1.3 (9H, s), 2.84 (2H, m), 3.55 (2H, m), 4.31 (2H, m), 4.43 (2H, m), 6.62-6.70 (2H, m), 6.91-7.2 (6H, m), 7.37 (2H, d, J=8.18)

EXAMPLE 8

1,2,3,4-Tetrahydro-quinoline-8-carboxylic acid (3,5-bis-trifluoromethyl-benzyl)-[2-(4-fluoro-phenyl)-ethyl]-amide 1.87 (2H, t, J=5.3), 2.74 (2H, t, J=6.12), 2.84-2.87 (2H, m), 3.27 (2H, t, J=5.19), 3.57 (2H, t, J=6.72), 4.61 (2H, m), 4.48 (1H, bs), 6.54 (1H, t, J=7.5), 6.81 (1H, d, J=7.47), 6.94-7.06 (4H, m), 7.66 (1H, s), 7.78 (1H, s)

EXAMPLE 9

1,2,3,4-Tetrahydro-quinoline-8-carboxylic acid (4-tert-butyl-benzyl)-(3-phenoxy-phenyl)-amide 1.29 (9H, m), 1.80 (2H, m), 2.70 (2H, m), 3.27 (2H, m), 5.05 (2H,s), 5.92 (1H, s), 6.21 (1H, t, J=7.47, 14.5), 6.57-6.66 (4H, m), 6.81 (3H, m), 7.03 (1H, m), 7.14-7.31 (7H, m)

EXAMPLE 10

1,2,3,4-Tetrahydro-quinoline-8-carboxylic acid (4-tert-butyl-benzyl)-[2-(3-chloro-phenyl)-ethyl]-amide 1.31 (9H, s), 1.89 (2H, t), 2.75 (2H, t), 2.83 (9H, brs), 3.28 (2H, brs), 3.55 (2H, brs), 4.48 (2H, brs), 4.86 (1H, s), 6.51 (1H, t), 6.90 (1H, q), 7.17 (3H, brt, J=7.17)

EXAMPLE 11

2,3,6,7,8,9-Hexahydro-1H-6-aza-cyclopenta[a]naphthalene-5-carboxylic acid (4-tert-butyl-benzyl)-[2-(4-fluoro-phenyl)-ethyl]-amide 1.30 (9H, m), 1.89-2.03 (4H, m), 2.62 (2H, t, J=7.02, 13.92), 3.23 (2H, t, J=4.94, 10.08), 3.54 (2H, m), 4.70 (2H,s), 5.29 (1H,s), 6.72 (1H, s), 6.94 (2H, t, J=8.58), 7.0 (2H,m), 7.15 (2H, d, J=7.47), 7.34 (2H, d, J=8.16)

EXAMPLE 12

6-Methoxy-1,2,3,4-tetrahydro-quinoline-8-carboxylic acid (4-tert-butyl-benzyl)-[2-(4-fluoro-phenyl)-ethyl]-amide 1.23 (9H, s), 1.80 (2H, t, J=5.19), 2.62 (2H,t, J=6.15), 2.79 (2H, s), 3.15 (2H, t, J=5.19), 3.48 (4H, s), 4.38 (1H, s), 6.36 (1H, s), 6.48 (1H, s), 6.48 (1H, s), 6.85 (2H, t, J=7.86), 7.05 (4H, m), 7.26 (2H, d, J=7.98)

EXAMPLE 13

6-Methyl-1,2,3,4-tetrahydro-quinoline-8-carboxylic acid (4-tert-butyl-benzyl)-[2-(4-fluoro-phenyl)-ethyl]-amide 1.31 (9H,m), 1.87 (2H, m), 2.12 (3H, s), 2.73 (2H, m), 2.83 (2H, m), 3.24 (2H, m), 3.50 (2H, m), 4.54 (2H, m), 6.63 (1H, s), 6.74 (1H, s), 6.94-7.36 (8H, m)

EXAMPLE 14

1,2,3,4-Tetrahydro-quinoline-8-carboxylic acid [2-(4-fluoro-phenyl)-ethyl]-(4-trifluoromethyl-benzyl)-amide 1.89 (2H, t), 2.75 (2H, t), 3.28 (2H, brs), 3.56 (2H, t), 4.58 (2H, brs), 4.87 (1H, brs), 6.49 (1H, t), 6.84 (2H, d), 6.95 (3H, t), 7.05 (1H, s), 7.26 (2H, brs), 7.27 (2H, brd), 7.58 (2H, d)

EXAMPLE 15

1,2,3,4-Tetrahydro-quinoline-8-carboxylic acid (4-diethylamino-benzyl)-[2-(4-fluoro-phenyl)-ethyl]-amide 1.15 (6H, t, J=6.96), 1.89 (2H, m), 2.72-2.82 (4H, m), 3.27 (2H, m), 3.32 (4H, q, J=6.75), 3.49-3.54 (2H, m), 4.39 (2H, brs), 4.76 (1H, brs), 6.48 (1H, t, J=7.44), 6.62 (2H, d, J=8.48), 6.48-7.04 (7H, m)

EXAMPLE 16

1,2,3,4-Tetrahydro-quinoline-8-carboxylic acid (4-tert-butyl-benzyl)-[2-(4-chloro-phenyl)-ethyl]-amide 1.31 (9H, s), 1.89 (2H, m), 2.72-2.82 (4H, m), 3.27 (2H, m), 3.35 (2H, m), 4.48 (2H, brs), 4.81 (1H, brs), 6.48 (1H, t, J=7.44), 6.48-6.92 (2H, m), 7.14-7.7.22 (4H, m). 7.33-7.36 (4H, m)

EXAMPLE 17

1,2,3,4-Tetrahydro-quinoline-8-carboxylic acid (4-tert-butyl-benzyl)-[2-(4-methoxy-phenyl)-ethyl]-amide 1.30 (9H, s), 1.88 (2H, m), 2.74 (4H, m), 3.26 (2H, m), 3.55 (2H, m), 3.77 (2H, m), 4.77 (2H, m), 6.82-6.88 (5H, m), 7.32-7.35 (2H, m)

EXAMPLE 18

1,2,3,4-Tetrahydro-quinoline-8-carboxylic acid (4-tert-butyl-benzyl)-[2-(2,6-dichloro-phenyl)-ethyl]-amide 1.30 (9H,m), 1.90 (2H, m), 2.75 (2H, t, J=6.03), 3.29-3.49 (4H, m), 4.70 (2H, brs), 6.51 (1H, t, J=7.5, 14.85), 6.90-6.97 (3H, m), 7.04-7.2 (4H, m), 7.33 (3H, d, J=7.35)

EXAMPLE 19

1,2,3,4-Tetrahydro-quinoline-8-carboxylic acid (4-tert-butyl-benzyl)-(4-fluoro-benzyl)-amide 1.33 (9H, s), 1.90 (2H, t, J=5.4), 2.74 (2H, t, J=6.3), 3.32 (2H, t, J=5.4), 4.52 (4H, m), 6.46 (1H, m), 6.94 (4H, m), 6.99 (4H, m), 7.37 (2H, d, J=6.69)

EXAMPLE 20

1,2,3,4-Tetrahydro-quinoline-8-carboxylic acid (4-tert-butyl-benzyl)-[2-(3,4-dichloro-phenyl)-ethyl]-amide 1.31 (9H, m), 1.89 (2H, t, J=5.19), 2.75 (4H, m), 3.30 (2H, t, J=4.98), 3.55 (2H, m), 4.50 (2H, s), 4.88 (1H, s), 6.48 (1H, t, J=7.41), 6.90 (3H, m), 7.15 (3H, m), 7.34 (3H, m)

EXAMPLE 21

1,2,3,4-Tetrahydro-quinoline-8-carboxylic acid (4-tert-butyl-benzyl)-(3-chloro-benzyl)-amide 1.32 (9H, s), 1.90-1.94 (2H, m), 2.76 (2H, t, J=6.21), 3.35 (2H, m), 4.52 (2H, bs), 5.12 (2H, bs), 6.48 (1H, t, J=7.5), 6.91-6.97 (2H, m), 7.12-7.15 (3H, m), 7.36 (2H, d, J=8.13)

EXAMPLE 22

1,2,3,4-Tetrahydro-quinoline-8-carboxylic acid (4-tert-butyl-benzyl)-[2-(2-fluoro-phenyl)-ethyl]-amide 1.30 (9H, s), 1.85 (2H, t, J=6.03), 2.72 (2H, t, J=6.21), 2.94 (2H, s), 3.26 (2H, t, J=5.37), 3.58 (2H, s), 4.49 (1H, s), 4.85 (1H,s), 6.45 (1H, t, J=7.44), 6.84 (2H, dd, J=7.41 & 14.37), 6.97 (2H, m), 7.15 (3H, m), 7.32 (2H, d, J=8.07)

EXAMPLE 23

1,2,3,4-Tetrahydro-quinoline-8-carboxylic acid [2-(3,5-bis-trifluoromethyl-phenyl)-ethyl]-(4-tert-butyl-benzyl)-amide 1.31 (9H, s), 1.88 (2H, t, J=5.4), 2.74 (2H, t, J=6.09), 2.96 (2H, m), 3.31 (2H, m), 3.57 (2H, t, J=6.9), 4.52 (2H, s), 4.98 (1H,s), 6.48 (1H, t, J=7.29), 6.8 (1H, d, J=7.35), 6.93 (1H, d, J=7.23), 7.14 (2H, d, J=7.41), 7.26 (2H, d, J=8.01), 7.51 (1H, s), 7.71 (1H, s)

EXAMPLE 24

6-Fluoro-1,2,3,4-tetrahydro-quinoline-8-carboxylic acid (4-tert-butyl-benzyl)-[2-(4-fluoro-phenyl)-ethyl]-amide 1.31 (9H,m), 1.87 (2H, m), 2.73 (4H, t, J=6.06), 2.83 (2H, s), 3.24 (2H, t, J=5.34), 3.55 (2H, m), 4.47 (2H, s), 6.57(2H, m), 6.67 (3H,m), 7.12 (3H, m), 7.35 (2H, d, J=8.1)

EXAMPLE 25

6-Chloro-1,2,3,4-tetrahydro-quinoline-8-carboxylic acid (4-tert-butyl-benzyl)-[2-(4-fluoro-phenyl)-ethyl]-amide 1.31 (9H, s), 1.86 (2H, t, J=5.58), 2.71 (2H, t, J=6.2), 2.83 (2H, s), 3.24 (2H, m), 3.54 (3H, m), 4.48 (2H, s), 4.72 (1H, s), 6.78 (1H, d, J=2.31), 6.96 (2H, m), 7.12 (4H, m), 7.35 (2H, d, J=8.16)

EXAMPLE 26

1,2,3,4-Tetrahydro-quinoline-8-carboxylic acid (4-tert-butyl-benzyl)-phenethyl-amide 1.30

(9H, m), 1.88 (2H, m), 2.74 (2H, t, J=6.21, 12.45), 2.88 (2H, s), 3.26 (2H, t, J=5.4), 3.57 (2H, s), 4.47 (2H, m), 4.80 (1H, s), 6.48 (1H, t, J=7.53), 6.88 (2H, m), 7.13 (3H, m), 7.34 (2H, d, J=8.13)

EXAMPLE 27

6-Bromo-1,2,3,4-tetrahydro-quinoline-8-carboxylic acid (4-tert-butyl-benzyl)-[2-(3-chloro-phenyl)-ethyl]-amide 1.32 (9H, s), 1.87 (2H, m), 2.7 (2H, m), 2.83 (2H, m), 3.26 (2H, m), 3.5 (2H, m), 4.46 (2H, m), 4.79 (1H, s), 6.94-7.2 (5H, m), 7.26-7.39 (5H, m)

EXAMPLE 28

1,2,3,4-Tetrahydro-quinoline-8-carboxylic acid (4-tert-butyl-benzyl)-[2-(4-diethylamino-phenyl)-ethyl]-amide 1.10 (6H, t, J=7.05), 1.12 (9H, s), 1.88 (2H, m), 2.73 (2H, m), 3.27.3.34 (5H, m), 3.49 (2H, m), 6.48-6.60 (2H, m), 6.89 (2H, d, J=7.53), 7.15 (2H, m), 7.34 (2H, d, J=8.04)

EXAMPLE 29

1,2,3,4-Tetrahydro-quinoline-8-carboxylic acid [2-(3,4-dichloro-phenyl)-ethyl]-(4-methyl-benzyl)-amide 1.87-1.91 (2H, m), 2.34 (3H, s), 2.73-2.77 (4H, m), 3.2 (2H, m), 3.5 (2H, m), 4.49 (2H, m), 5.3 (1H, m), 6.4 (1H, m), 6.84-6.93 (3H, m), 7.1-(3H, m), 7.3 (2H,m)

EXAMPLE 30

1,2,3,4-Tetrahydro-quinoline-8-carboxylic acid [2-(4-bromo-phenyl)-ethyl]-(4-tert-butyl-benzyl)-amide 1.31 (9H, s), 1.89 (2H, t, J=5.73), 2.72 (2H, t, J=6.12), 2.82 (2H, s), 3.26 (2H, t, J=5.34), 3.55 (2H, s), 4.49 (1H, s), 4.83 (1H, s), 6.45 (1H, t, J=7.38), 6.84 (2H, m), 6.98 (1H, m), 7.14 (2H, s), 7.33 (4H, t, J=8.4)

EXAMPLE 31

6-Methyl-1,2,3,4-tetrahydro-quinoline-8-carboxylic acid (4-tert-butyl-benzyl)-[2-(3,4-dichloro-phenyl)-ethyl]-amide 1.57 (9H, s), 1.90 (2H, t), 2.13 (3H, s), 2.70 (2H, t), 2.74 (2H, brt), 3.24 (2H, t), 3.54 (2H, brt), 4.48 (2H, brs), 4.52 (1H, brs), 6.63 (1H, brs), 6.75 (1H, brs), 6.94 (1H, brs), 7.15 (3H, m), 7.34 (4H, brt)

EXAMPLE 32

6-Fluoro-1,2,3,4-tetrahydro-quinoline-8-carboxylic acid (4-tert-butyl-benzyl)-[2-(3,4-dichloro-phenyl)-ethyl]-amide 1.31 (9H,m), 1.90 (2H, m), 2.73 (2H, t, J=6.27), 2.80 (2H, s), 3.25 (2H, t, J=5.12), 3.55 (2H, m), 4.5 (3H, m), 6.58 (1H, m), 6.95 (1H, bs), 7.12 (3H, m), 7.35 (3H, m)

EXAMPLE 33

1,2,3,4-Tetrahydro-quinoline-8-carboxylic acid [2-(4-fluoro-phenyl)-ethyl]-naphthalen-2-ylmethyl-amide 1.88-1.91 (2H, m), 2.73-2.77 (2H, m), 2.87 (2H, m), 3.30 (2H, m), 3.60 (2H, m), 4.67 (2H, m), 4.89 (1H, m), 6.48 (1H, t), 6.88-6.97 (8H, m), 7.47-7.50 (2H, m), 7.65 (1H, m), 7.79-7.83 (3H, m)

EXAMPLE 34

6-Chloro-1,2,3,4-tetrahydro-quinoline-8-carboxylic acid (2-benzo[1,3]dioxol-5-yl-ethyl)-(4-tert-butyl-benzyl)-amide 1.31 (9H, s), 1.85-1.88 (2H, m), 2.99-2.73 (3H, m), 3.26 (2H, m), 3.48-3.50 3H, m), 4.49 (2H, bs), 4.74 (1H, s), 5.92 (2H, s), 6.58 (2H, m), 6.71-6.73 (1H, m), 6.79 (1H, s), 6.89 (1H, s), 7.14 (2H, m), 7.29-7.37 (2H, m)

EXAMPLE 35

6-Chloro-1,2,3,4-tetrahydro-quinoline-8-carboxylic acid (4-tert-butyl-benzyl)-[2-(3,4-dichloro-phenyl)-ethyl]-amide 1.25 (9H, s), 1.71 (2H, t), 2.65 (2H, t), 2.71 (2H, t), 2.81 (2H, t), 3.13 (2H, t), 4.41 (2H, t), 6.61(1H, brs), 6.93 (2H, brs), 7.19 (2H, brs), 7.34 (2H, brd), 7.48 (2H, brd)

EXAMPLE 36

1,2,3,4-Tetrahydro-quinoline-8-carboxylic acid (4-tert-butyl-benzyl)-(2-naphthalen-2-yl-ethyl)-amide 1.31 (9H, s), 1.81-1.84 (2H, m), 2.69-2.73 (2H, m), 3.09-3.11 (4H, m), 3.48 (1H, bs), 3.68 (1H, bs), 4.72 (1H, bs), 6.46-6.48 (1H, m), 6.86-6.91 2H, m), 7.13 (1H, m), 7.33-7.48 (4H, m), 7.74-7.81 3H, m)

EXAMPLE 37

1,2,3,4-Tetrahydro-quinoline-8-carboxylic acid (4-tert-butyl-benzyl)-(2-naphthalen-1-yl-ethyl)-amide 1.30 (9H, s), 1.90 (2H, m), 2.78 (2H, m), 3.31 (4H, m), 3.48-3.50 (4H, m), 6.50 (2H, m), 6.91 (1H, m), 7.32-7.79 (8H, m)

EXAMPLE 38

1,2,3,4-Tetrahydro-quinoline-8-carboxylic acid (2-benzo[1,3]dioxol-5-yl-ethyl)-(4-tert-butyl-benzyl)-amide 1.30 (9H, s), 1.87-1.91 (2H, m), 2.72-2.77 (4H, m), 3.28 (2H, m), 3.48-3.50 (4H, m), 4.49 (2H, m), 5.91 (2H, s), 6.49-6.72 (3H, m), 6.87-6.92 (2H, m), 7.15 (2H, m), 7.33-7.36 (2H, m)

EXAMPLE 39

1,2,3,4-Tetrahydro-quinoline-8-carboxylic acid (4-tert-butyl-benzyl)-indan-5-yl-amide 1.29 (9H, m), 1.89 (2H, m), 2.0 (2H, t, J=7.23), 2.71 (2H, m), 2.76 (4H, m), 3.34 (2H, m), 3.48 (1H, m), 5.03 (2H, s), 5.97 (1H, m), 6.14 (1H, t, J=7.5), 6.67-6.76 (3H, m), 6.89 (1H, s), 6.91 (1H, d, J=8.07), 7.32 (3H, m)

EXAMPLE 40

6-Chloro-1,2,3,4-tetrahydro-quinoline-8-carboxylic acid (4-tert-butyl-benzyl)-[2-(3,4-difluoro-phenyl)-ethyl]-amide 1.31 (9H, m), 1.87 (2H, m), 2.72 (2H, t, J=6.24), 2.79 (2H, t), 3.26 (2H, t, J=5.37), 3.54 (2H, m), 4.5 (2H, s), 6.79 (2H, m), 6.90 (1H, m), 7-7.15 (4H,m), 7.36 (2H, d, J=8.19)

EXAMPLE 41

1,2,3,4-Tetrahydro-quinoline-8-carboxylic acid (4-tert-butyl-benzyl)-[2-(3,4-difluoro-phenyl)-ethyl]-amide 1.31 (9H, m), 1.90 (2H, t, J=5.58), 2.77 (4H, m), 3.29 (2H, d, J=5.34), 3.54 (2H, t, J=7.32), 4.5 (2H, s), 6.49 (1H, t, J=7.41), 6.86 (1H, d, J=7.47), 6.92 (3H, d, J=7.83), 7.01 (1H, m), 7.14 (2H, d, J=6.75), 7.36 (2H, d, J=8.25)

EXAMPLE 42

1,2,3,4-Tetrahydro-quinoline-8-carboxylic acid (4-tert-butyl-benzyl)-[2-(4-hydroxy-phenyl)-ethyl]-amide 1.30 (9H, s), 1.88 (2H, m), 2.73 (3H, m), 3.26 (2H, m), 3.55 (3H, m), 4.73 (1H, s), 6.47 (2H, m), 6.74 (2H, m), 6.82-6.91 (2H, m) 7.33-7.35 (2H, m)

EXAMPLE 43

1,2,3,4-Tetrahydro-quinoline-8-carboxylic acid (4-tert-butyl-benzyl)-[2-(3,4-dimethoxy-phenyl)-ethyl]-amide 1.5 (9H, s), 1.87 (2H, t, J=5.49), 2.72 (2H, t, J=6.3), 2.82 (2H, s), 3.24 (2H, t, J=5.31), 3.57 (2H, s), 3.82 (3H, s), 3.85

(3H, s), 4.48 (2H, s), 4.79 (1H, s), 6.46 (1H, t, J=7.5), 6.67 (s, 1H), 6.76 (2H, d, J=7.35), 6.87 (2H, t, J=7.26), 7.15 (2H, s), 7.33 (2H, d, J=8.07)

EXAMPLE 44

1,2,3,4-Tetrahydro-quinoline-8-carboxylic acid (4-tert-butyl-benzyl)-[3-(4-fluoro-phenyl)-propyl]-amide 1.31 (9H, s), 1.88 (4H, m), 2.49 (2H, s), 2.73 (2H, t, J=6.24), 3.28 (4H, m), 4.59 (2H, s), 6.45 (1H, t, J=7.47), 6.88 (4H, t, J 7.68), 7.00 (2H, s), 7.12 (2H, d, J=7.74), 7.32(2H, d, J=8.1)

EXAMPLE 45

6-Chloro-1,2,3,4-tetrahydro-quinoline-8-carboxylic acid (4-tert-butyl-benzyl)-[2-(4-chloro-3-fluoro-phenyl)-ethyl]-amide 1.31 (9H, s), 1.85 (2H, t, J=5.22), 2.69 (2H, t, J=6.24), 2.81 (2H, s), 3.24 (2H, t, J=5.64), 3.55 (2H, s), 4.5 (2H, s), 4.75 (1H, s), 6.79 (4H, m), 7.15 (2H, s), 7.35 (3H, t, J=8.13)

EXAMPLE 46

6-Chloro-1,2,3,4-tetrahydro-quinoline-8-carboxylic acid (4-tert-butyl-benzyl)-[2-(3,5-dimethoxy-phenyl)-ethyl]-amide 1.31 (9H, s), 1.56 (6H, s), 1.84 (2H, t, J=5.16), 2.28 (6H, s), 2.68 (2H, t, J=5.88), 3.22 (2H, t, J=5.13), 3.53 (1H, s), 6.80 (2H, s), 6.85 (3H, d, J=8.61), 7.71 (1H, s), 7.33 (2H, d, J=7.8)

EXAMPLE 47

1,2,3,4-Tetrahydro-quinoline-8-carboxylic acid (4-tert-butyl-benzyl)-[2-(4-trimethylsilanyloxy-phenyl)-ethyl]-amide 0.2415 (9H, s], 1.25 (9H, s), 1.89 (2H, m), 2.72-2.81 (4H, m), 3.28 (2H, m), 3.53 (2H, m), 4.45 (2H, m), 4.85 (2H, m), 6.47 (2H, t, J=7.26), 7.6.73-6.75 (2H, m), 6.84-7.12 (6H, m), 7.33 (2H, d, J=7.95)

EXAMPLE 48

1,2,3,4-Tetrahydro-quinoline-8-carboxylic acid (4-tert-butyl-benzyl)-[2-(3,4-dichloro-phenyl)-ethyl]-amide; hydrochloride salt (Identity of the compound confirmed by HPLC; HCl salt of compound of example no. 17).

EXAMPLE 49

6-Methyl-1,2,3,4-tetrahydro-quinoline-8-carboxylic acid (4-tert-butyl-benzyl)-[2-(3,4-dichloro-phenyl)-ethyl]-amide; hydrochloride salt 1.26 (9H, s), 1.60 (2H, t), 2.08 (3H, s), 2.63 (2H, t), 2.64 (2H, brt), 3.16 (2H, t), 4.48 (2H, brt), 4.52 (2H, brt), 6.50 (1H, s), 6.63 (1H, s), 6.76 (1H, s), 6.94 (1H, brs), 7.21 (3H, m), 7.20 (3H, brt)

EXAMPLE 50

6-Fluoro-1,2,3,4-tetrahydro-quinoline-8-carboxylic acid (4-tert-butyl-benzyl)-[2-(3,4-dichloro-phenyl)-ethyl]-amide; hydrochloride salt (Identity of the compound confirmed by HPLC; HCl salt of compound of example no. 32)

EXAMPLE 51

6-Chloro-1,2,3,4-tetrahydro-quinoline-8-carboxylic acid (4-tert-butyl-benzyl)-[2-(3,4-difluoro-phenyl)-ethyl]-amide; hydrochloride salt 1.25 (9H, s), 1.71 (2H, t), 2.65 (2H, t), 2.71 (2H, brt), 2.81 (2H, t), 3.13 (2H, t), 4.41 (2H, br t), 6.61 (1H, brs), 6.93 (2H, brs), 7.19 (2H, brs), 7.34 (2H, brd), 7.48 (2H, brd)

EXAMPLE 52

6-Chloro-1,2,3,4-tetrahydro-quinoline-8-carboxylic acid (4-tert-butyl-benzyl)-[3-(3,4-dichloro-phenyl)-propyl]-amide; hydrochloride salt (Identity of the compound confirmed by HPLC; HCl salt of compound of example no. 35)

EXAMPLE 53

6-Chloro-1,2,3,4-tetrahydro-quinoline-8-carboxylic acid (4-tert-butyl-benzyl)-[2-(4-chloro-3-fluoro-phenyl)-ethyl]-amide; hydrochloride salt 1.61 (9H, s), 1.71 (2H, s), 2.63 (2H, s), 2.81 (2H, s), 3.15 (2H, s), 3.43 (2H, s), 4.43 (2H, s), 6.59 (1H, s), 6.92 (2H, s), 7.19 (2H, s), 7.34 (3H, t, J=7.74), 7.45 (2H, s)

EXAMPLE 54

6-Chloro-1,2,3,4-tetrahydro-quinoline-8-carboxylic acid (4-tert-butyl-benzyl)-[2-(3-chloro-4-fluoro-phenyl)-ethyl]-amide; hydrochloride salt 1.25 (9H, s), 1.71 (2H, s), 2.65 (2H, s), 2.78 (2H, s), 3.15 (2H, s), 3.64 (2H, s), 4.46 (2H, s), 6.62 (1H, s), 6.92 (1H, s), 7.28 (7H, m)

EXAMPLE 55

N-(4-tert-Butyl-benzyl)-2-dimethylamino-N-[2-(4-fluoro-phenyl)-ethyl]-3-methyl-benzamide 1.30 (9H, d, J=5.16), 2.32 (3H, d, J=5.94), 2.74 (1H, m), 2.83 (3H, s), 2.90-2.26 (3H, m), 4.09-4.25 (2H, m), 4.36-5.38 (1H, m), 6.76-6.83 (1H, m), 6.83 (2H, m), 6.98 (1H, m), 7.05 (3H, m), 7.15 (2H, m), 7.31-7.45 (2H, m).

EXAMPLE 56

N-(4-Tert-Butyl-benzyl)-2-(cyclohexylmethyl-amino)-N-[2-(4-fluoro-phenyl)-ethyl]-benzamide 0.99 (3H, m), 1.30 (12H, m), 1.80 (6H, m), 2.90 (4H, m), 4.50 (2H, m), 4.88 (2H, m), 5.30 (1H, m), 6.60 (2H, m), 6.97 (4H, m), 7.18 (4H,m), 7.31 (2H, m).

EXAMPLE 57

1,2,3,4-Tetrahydro-quinoline-8-sulfonic acid (4-tert-butyl-benzyl)-[2-(4-fluoro-phenyl)-ethyl]-amide 1.31 (9H, s), 1.90 (2H, m), 2.66 (2H, t, J=8.20), 2.66 (2H, t, J=6.20), 3.26-3.33 (4H, m), 4.30 (2H, s), 6.19 (1H, brs), 6.25 (1H, m), 6.84-6.90 (4H, m), 7.06-7.14 (3H, m), 7.30-7.38 (2H, m), 8.48 (1H, d, J=7.95).

Biological Data:
CETP in-vitro Assay

This assay used a commercially available Scintillation Proximity Assay kit (Amersham TRKQ7015) with modifications for measuring CETP activity. [$^3$H] Cholesteryl ester HDL was mixed with non radioactive HDL prepared from human plasma at an appropriate ratio in order to ensure a proper transfer of cholesteryl esters. Transfer of [$^3$H] Cholesteryl esters from high density lipoprotein (HDL) to biotinylated low density lipoprotein (LDL) was measured following incubation of donor and acceptor particles in the presence of recombinant CETP. Following overnight incubation, the reaction was terminated and transfer was measured in a single step addition of streptavidin coated beads formulated in an assay terminal buffer. The rate of increase in signal was proportional to the transfer of [$^3$H] Cholesteryl ester by CETP.

The following table shows the CETP inhibition of selected compounds at 10 μmole concentration.

| Compound No. | % of CETP inhibition at 10 μmole concentration |
|---|---|
| 1 | 43 |
| 7 | 67 |
| 10 | 57 |
| 13 | 80 |
| 14 | 74 |
| 17 | 92 |
| 21 | 77 |
| 22 | 94 |
| 24 | 76 |
| 28 | 80 |
| 29 | 83 |
| 31 | 82 |
| 32 | 82 |
| 35 | 85 |
| 37 | 86 |
| 38 | 78 |
| 40 | 89 |
| 42 | 99 |
| 43 | 80 |
| 45 | 88 |
| 47 | 76 |
| 48 | 79 |
| 50 | 90 |

The following table shows the measured IC$_{50}$ values for the selected compounds for its CETP inhibition in human plasma.

| Compound No. | IC$_{50}$ (nM) |
|---|---|
| 22 | 455 |
| 47 | 167 |
| 50 | 30 |

No adverse or serious side effects were observed with the compounds of the present invention.

We claim:
1. Compound represented by the formula (1)

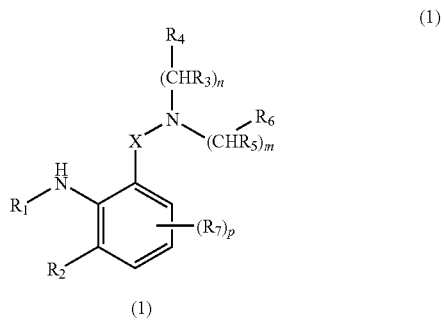

(1)

wherein
X is selected from C═O; R$_1$ and R$_2$ may, together along with the atoms to which they are attached, form a 6 membered heterocyclic ring having 1 heteroatoms selected from N; R$_3$ at each occurrence is independently an H atom; R$_4$ is selected from an optionally substituted C$_{(3-13)}$ carbocyclic or a heterocyclic residue; R$_5$ at each occurrence is independently an H atom; R$_6$ is selected from hydrogen, optionally substituted C$_{(3-13)}$ carbocyclic or a heterocyclic residue; R$_7$ at each occurrence is independently selected from the group consisting of hydrogen, halogen, optionally substituted groups selected from C$_{(1-6)}$ alkyl, lower halo C$_{(1-6)}$ alkyl groups; and m=1-2, n=2, p=0-3.

2. A compound as claimed in claim 1 wherein, "carbocycle or carbocyclic residue" include, phenyl, naphthyl, indanyl, or tetrahydronaphthyl (tetralin).

3. A compound as claimed in claim 1 wherein, "heterocycle or heterocyclic system" include, but are not limited to, benzoxazolyl, tetrahydroisoquinolinyl, tetrahydroquinolinyl.

4. A compound as claimed in claim 1 wherein X is selected from C═O; R$_1$ and R$_2$ may together along with the atoms to which they are attached form a 6 membered heterocyclic ring having 1-heteroatoms selected from N; R$_3$ & R$_5$ independently represent H; R$_4$ is selected from an optionally substituted aryl group; R$_5$ is H; R$_6$ is selected from an optionally substituted aryl group; R$_7$ at each occurrence is independently selected from the groups comprising of hydrogen, halogen, optionally substituted groups selected from C$_{(1-3)}$ alkyl group.

5. A compound as claimed in claim 1, wherein R$_1$ & R$_2$ together forms an optionally substituted heterocyclic groups selected from 1,2,3,4-tetrahydro-quinoline.

6. A compound as claimed in claim 1 wherein R$_4$ & R$_6$ are each an optionally substituted phenyl group.

7. A compound as claimed in claim 1 further comprising:
1,2,3,4-Tetrahydro-quinoline-8-carboxylic acid (4-tert-butyl-benzyl)-(2-(4-fluoro-phenyl)-ethyl)-amide;
6-Trifluoromethyl-1,2,3,4-tetrahydro-quinoline-8-carboxylic acid (4-tert-butyl-benzyl)-(2-(4-fluoro-phenyl)-ethyl)-amide;
5-Trifluoromethyl-1,2,3,4-tetrahydro-quinoline-8-carboxylic acid (4-tert-butyl-benzyl)-(2-(4-fluoro-phenyl)-ethyl)-amide;
5-Chloro-1,2,3,4-tetrahydro-quinoline-8-carboxylic acid (4-tert-butyl-benzyl)-(2-(4-fluoro-phenyl)-ethyl)-amide;
1,2,3,4-Tetrahydro-quinoline-8-carboxylic acid (3,5-bis-trifluoromethyl-benzyl)-(2-(4-fluoro-phenyl)-ethyl)-amide;

1,2,3,4-Tetrahydro-quinoline-8-carboxylic acid (4-tert-butyl-benzyl)-(3-phenoxy-phenyl)-amide;
1,2,3,4-Tetrahydro-quinoline-8-carboxylic acid (4-tert-butyl-benzyl)-(2-(3-chloro-phenyl)-ethyl)-amide;
6-Methyl-1,2,3,4-tetrahydro-quinoline-8-carboxylic acid (4-tert-butyl-benzyl)-(2-(4-fluoro-phenyl)-ethyl)-amide;
1,2,3,4-Tetrahydro-quinoline-8-carboxylic acid (2-(4-fluoro-phenyl)-ethyl)-(4-trifluoromethyl-benzyl)-amide;
1,2,3,4-Tetrahydro-quinoline-8-carboxylic acid (4-diethylamino-benzyl)-(2-(4-fluoro-phenyl)-ethyl)-amide;
1,2,3,4-Tetrahydro-quinoline-8-carboxylic acid (4-tert-butyl-benzyl)-(2-(4-methoxy-phenyl)-ethyl)-amide;
1,2,3,4-Tetrahydro-quinoline-8-carboxylic acid (4-tert-butyl-benzyl)-(2-(2,6-dichloro-phenyl)-ethyl)-amide;
1,2,3,4-Tetrahydro-quinoline-8-carboxylic acid (4-tert-butyl-benzyl)-(4-fluoro-benzyl)-amide;
1,2,3,4-Tetrahydro-quinoline-8-carboxylic acid (4-tert-butyl-benzyl)-(2-(3,4-dichloro-phenyl)-ethyl)-amide;
1,2,3,4-Tetrahydro-quinoline-8-carboxylic acid (4-tert-butyl-benzyl)-(3-chloro-benzyl)-amide;
1,2,3,4-Tetrahydro-quinoline-8-carboxylic acid (4-tert-butyl-benzyl)-(2-(2-fluoro-phenyl)-ethyl)-amide;
1,2,3,4-Tetrahydro-quinoline-8-carboxylic acid (2-(3,5-bis-trifluoromethyl-phenyl)-ethyl)-(4-tert-butyl-benzyl)-amide;
6-Fluoro-1,2,3,4-tetrahydro-quinoline-8-carboxylic acid (4-tert-butyl-benzyl)-(2-(4-fluoro-phenyl)-ethyl)-amide;
6-Chloro-1,2,3,4-tetrahydro-quinoline-8-carboxylic acid (4-tert-butyl-benzyl)-(2-(4-fluoro-phenyl)-ethyl)-amide;
1,2,3,4-Tetrahydro-quinoline-8-carboxylic acid (4-tert-butyl-benzyl)-phenethyl-amide;
6-Bromo-1,2,3,4-tetrahydro-quinoline-8-carboxylic acid (4-tert-butyl-benzyl)-(2-(3-chloro-phenyl)-ethyl)-amide;
1,2,3,4-Tetrahydro-quinoline-8-carboxylic acid (4-tert-butyl-benzyl)-(2-(4-diethylamino-phenyl)-ethyl)-amide;
1,2,3,4-Tetrahydro-quinoline-8-carboxylic acid (2-(3,4-dichloro-phenyl)-ethyl)-(4-methyl-benzyl)-amide;
1,2,3,4-Tetrahydro-quinoline-8-carboxylic acid (2-(4-bromo-phenyl)-ethyl)-(4-tert-butyl-benzyl)-amide;
6-Methyl-1,2,3,4-tetrahydro-quinoline-8-carboxylic acid (4-tert-butyl-benzyl)-(2-(3,4-dichloro-phenyl)-ethyl)-amide;
6-Fluoro-1,2,3,4-tetrahydro-quinoline-8-carboxylic acid (4-tert-butyl-benzyl)-(2-(3,4-dichloro-phenyl)-ethyl)-amide;
1,2,3,4-Tetrahydro-quinoline-8-carboxylic acid (2-(4-fluoro-phenyl)-ethyl)-naphthalen-2-ylmethyl-amide;
1,2,3,4-Tetrahydro-quinoline-8-carboxylic acid (4-tert-butyl-benzyl)-(2-(3,4-dichloro-phenyl)-ethyl)-amide hydrochloride;
6-Chloro-1,2,3,4-tetrahydro-quinoline-8-carboxylic acid (4-tert-butyl-benzyl)-(2-(4-fluoro-phenyl)-ethyl)-amide hydrochloride;
6-Methyl-1,2,3,4-tetrahydro-quinoline-8-carboxylic acid (4-tert-butyl-benzyl)-(2-(3,4-dichloro-phenyl)-ethyl)-amide hydrochloride;
6-Fluoro-1,2,3,4-tetrahydro-quinoline-8-carboxylic acid (4-tert-butyl-benzyl)-(2-(3,4-dichloro-phenyl)-ethyl)-amide hydrochloride;
6-Chloro-1,2,3,4-tetrahydro-quinoline-8-carboxylic acid (2-benzo(1,3)dioxol-5-yl-ethyl)-(4-tert-butyl-benzyl)-amide;
6-Chloro-1,2,3,4-tetrahydro-quinoline-8-carboxylic acid (4-tert-butyl-benzyl)-(2-(3,4-dichloro-phenyl)-ethyl)-amide hydrochloride;
6-Chloro-1,2,3,4-tetrahydro-quinoline-8-carboxylic acid (4-tert-butyl-benzyl)-(2-(3,4-dichloro-phenyl)-ethyl)-amide;
1,2,3,4-Tetrahydro-quinoline-8-carboxylic acid (4-tert-butyl-benzyl)-(2-naphthalen-2-yl-ethyl)-amide;
1,2,3,4-Tetrahydro-quinoline-8-carboxylic acid (4-tert-butyl-benzyl)-(2-naphthalen-1-yl-ethyl)-amide;
1,2,3,4-Tetrahydro-quinoline-8-carboxylic acid (2-benzo(1,3)dioxol-5-yl-ethyl)-(4-tert-butyl-benzyl)-amide;
1,2,3,4-Tetrahydro-quinoline-8-carboxylic acid (4-tert-butyl-benzyl)-indan-5-yl-amide;
6-Chloro-1,2,3,4-tetrahydro-quinoline-8-carboxylic acid (4-tert-butyl-benzyl)-(2-(3,4-difluoro-phenyl)-ethyl)-amide;
1,2,3,4-Tetrahydro-quinoline-8-carboxylic acid (4-tert-butyl-benzyl)-(2-(3,4-difluoro-phenyl)-ethyl)-amide;
1,2,3,4-Tetrahydro-quinoline-8-carboxylic acid (4-tert-butyl-benzyl)-(2-(4-hydroxy-phenyl)-ethyl)-amide;
1,2,3,4-Tetrahydro-quinoline-8-carboxylic acid (4-tert-butyl-benzyl)-(2-(3,4-dimethoxy-phenyl)-ethyl)-amide;
1,2,3,4-Tetrahydro-quinoline-8-carboxylic acid (4-tert-butyl-benzyl)-(3-(4-fluoro-phenyl)-propyl)-amide;
6-Chloro-1,2,3,4-tetrahydro-quinoline-8-carboxylic acid (4-tert-butyl-benzyl)-(2-(4-chloro-3-fluoro-phenyl)-ethyl)-amide;
6-Chloro-1,2,3,4-tetrahydro-quinoline-8-carboxylic acid (4-tert-butyl-benzyl)-(2-(3,5-dimethoxy-phenyl)-ethyl)-amide;
6-Chloro-1,2,3,4-tetrahydro-quinoline-8-carboxylic acid (4-tert-butyl-benzyl)-(2-(3,4-difluoro-phenyl)-ethyl)-amide, hydrochloride;
6-Chloro-1,2,3,4-tetrahydro-quinoline-8-carboxylic acid (4-tert-butyl-benzyl)-(3-(3,4-dichloro-phenyl)-propyl)-amide hydrochloride salt;
1,2,3,4-Tetrahydro-quinoline-8-carboxylic acid (4-tert-butyl-benzyl)-(2-(4-trimethylsilanyloxy-phenyl)-ethyl)-amide;
6-Chloro-1,2,3,4-tetrahydro-quinoline-8-carboxylic acid (4-tert-butyl-benzyl)-(2-(4-chloro-3-fluoro-phenyl)-ethyl)-amide hydrochloride salt;
6-Chloro-1,2,3,4-tetrahydro-quinoline-8-carboxylic acid (4-tert-butyl-benzyl)-(2-(3-chloro-4-fluoro-phenyl)-ethyl)-amide hydrochloride salt;
6-Chloro-1,2,3,4-tetrahydro-quinoline-8-carboxylic acid 4-tert-butyl-benzylamide.

8. A compound as claimed in claim 2 wherein $R_1$ & $R_2$ together form an optionally substituted heterocyclic groups selected from 1,2,3,4-tetrahydro-quinoline.

9. A compound as claimed in claim 3 wherein $R_1$ & $R_2$ together form an optionally substituted heterocyclic groups selected from 1,2,3,4-tetrahydro-quinoline.

10. A compound as claimed in claim 2 wherein $R_4$ & $R_6$ are each an optionally substituted phenyl group.

11. A compound as claimed in claim 3 wherein $R_4$ & $R_6$ are each an optionally substituted phenyl group.

12. A compound as claimed in claim 4 wherein $R_4$ & $R_6$ are each an optionally substituted phenyl group.

13. A compound as claimed in claim 5 wherein $R_4$ & $R_6$ are each an optionally substituted phenyl group.

* * * * *